United States Patent [19]

Eveleigh

[11] Patent Number: 5,158,880
[45] Date of Patent: Oct. 27, 1992

[54] PROCESS FOR PREPARING SOLID PERFLUOROCARBON POLYMER SUPPORTS HAVING ATTACHED PERFLUOROCARBON-SUBSTITUTED LIGAND OR BINDER

[75] Inventor: John W. D. Eveleigh, Hockessin, Del.

[73] Assignee: E. I. Du Pont de Nemours and Company, Wilmington, Del.

[21] Appl. No.: 248,386

[22] Filed: Sep. 23, 1988

[51] Int. Cl.$^5$ .................. C12N 11/08; C07K 17/08
[52] U.S. Cl. .................. 435/180; 204/59 F; 204/82; 427/322; 427/338; 435/6; 435/4; 435/7.1; 435/7.5; 435/7.6; 435/7.92; 435/181; 436/501; 436/532; 436/126; 530/391.1; 935/86; 935/110
[58] Field of Search .............. 204/59 F, 82; 427/322, 427/338; 435/6, 7, 181, 4, 7.1, 7.5, 7.6, 7.92, 180; 436/501, 532, 126; 530/387; 935/86, 110

[56] References Cited

U.S. PATENT DOCUMENTS

| | | | |
|---|---|---|---|
| 3,843,443 | 10/1974 | Fishman | 195/63 |
| 3,966,580 | 6/1976 | Janata et al. | 204/195 B |
| 4,619,897 | 10/1986 | Hato et al. | 435/182 |
| 4,711,955 | 12/1987 | Ward et al. | 536/29 |
| 4,885,250 | 12/1989 | Eveleigh et al. | 435/181 |
| 4,954,444 | 9/1990 | Eveleigh et al. | 435/181 |

FOREIGN PATENT DOCUMENTS 8603840  7/1986  World Int. Prop. O. .

OTHER PUBLICATIONS

Kobos et al. (1988) Anal. Chem. vol. 60, pp. 1996–1998.

Primary Examiner—Margaret Moskowitz
Assistant Examiner—Ardin H. Marschel
Attorney, Agent, or Firm—Roseanne R. Duffy

[57] ABSTRACT

A process for preparing solid perfluorocarbon polymer supports permitting uniform and secure attachment of perfluorocarbon-substituted ligands or binders to carriers is provided utilizing pretreatment of the carriers with water miscible organic solvents.

4 Claims, No Drawings

PROCESS FOR PREPARING SOLID PERFLUOROCARBON POLYMER SUPPORTS HAVING ATTACHED PERFLUOROCARBON-SUBSTITUTED LIGAND OR BINDER

TECHNICAL FIELD

This invention relates to a process for preparing solid perfluorocarbon polymer supports and more specifically to a process permitting more efficient adsorption of perfluorocarbon-substituted ligands or binders to carriers for use in affinity separations.

BACKGROUND ART

Affinity separation is separation achieved by employing the specific binding of one molecule by another. Bioaffinity separation is defined as an affinity separation in which one of the components involved in an affinity reaction is biologically active or is of biological interest. Bioaffinity separations generally involve at least one biomacromolecule, such as a protein or nucleic acid, as one of the components of the binding pair. Examples of such bioaffinity binding pairs include: antigen-antibody, substrate-enzyme, effector-enzyme, complementary nucleic acid strands, and others; the terms ligand and binder will be used to represent the two components in specific bioaffinity binding pairs.

Affinity separations are often considered to require the use of solid supports derivatized with a ligand or binder. Such solid supports should have the following properties: physical and chemical stability; chemical inertness; compatibility with a variety of biological samples; utility in batch and chromatographic applications; ability to provide for ready and secure attachment of ligands and binders to the surface; and allow simple efficient regeneration of the support.

Solid perfluorocarbon polymer supports have been found to be especially effective as affinity supports. Applicant's assignee's, E. I. du Pont de Nemours & Co. U.S. Pat. Nos. 4,885,250 and 4,954,444, issued Dec. 5, 1989 and Jan. 5, 1990, respectively, disclose perfluorocarbon polymer supports to which perfluorocarbon-substituted ligands or binders have been attached. Such supports can be prepared by batch and chromatographic processes.

Perfluorocarbon polymer carrier surfaces are hydrophobic and adsorption of perfluorocarbon-substituted ligands and binders to these surfaces is made difficult by the inability to wet these surfaces with aqueous solutions. Upon contacting a perfluorocarbon polymer carrier with an aqueous solution containing a perfluorocarbon-substituted ligand or binder, it is believed that a layer of air is formed between the carrier surface and the aqueous solution causing the carrier to clump and float at the surface of the aqueous solution. The ligand or binder contained in such solution is unable to contact uniformly and adsorb to the carrier surface. Preparation of supports using only aqueous solutions can result in non-uniform and unsecure adsorption of ligands and binders on the support surfaces.

Treating perfluorocarbon polymer surfaces with organic solvents before adsorbing ligands and binders to these surfaces has been described. Janata et al. (U.S. Pat. No. 3,966,580, issued Jun. 29, 1976) disclose a protein-immobilizing hydrophobic polymeric membrane prepared by swelling the membrane with an organic solvent containing an aliphatic compound having a reactive site, drying the membrane to remove the solvent, and immersing the membrane in a solution containing a compound having both a reactive site which recognizes the reactive site of the aliphatic compound and a protein-reactive site. The membrane is then ready to be reacted with the protein to be immobilized. Lower molecular weight organic solvents are preferred so they can be readily removed.

Fishman (U.S. Pat. No. 3,843,443, issued Oct. 22, 1974) discloses two processes for preparing a bound polypeptide material. A porous unsintered fluorocarbon polymer is first flooded with a water-miscible organic solvent. The flooded fluorocarbon polymer is then contacted with an aqueous solution of polypeptide polyelectrolyte for a length of time sufficient to replace a portion of the organic solvent with the polypeptide polyelectrolyte. Alternatively, the solvent-flooded fluorocarbon polymer can be flooded with water prior to contacting it with the aqueous polypeptide polyelectrolyte solution. Neither process is suitable for preparing perfluorocarbon polymer supports. Since perfluorocarbon-substituted ligands and binders can be denatured by solutions containing a high concentration of water-miscible organic solvent, contacting an aqueous solution of such ligands or binders with a solvent-flooded carrier as in the first process can denature the ligands or binders. It is believed that when preparing a support using the second process, the carrier would become unwetted after flooding it with water and would float to the water surface. Subsequently contacting the carrier with an aqueous solution of a perfluorocarbon-substituted ligand or binder could result in non-uniform and non-secure adsorption of such ligand or binder.

WO 8603-840-A, published Jul. 3, 1986, discloses a process for treating a synthetic polymer to make it receptive to adsorption of an immunoreagent by thoroughly rinsing the polymer surface with a water-miscible organic solvent and then thoroughly rinsing the polymer surface with water. The solvent is used to clean the polymer surface before contacting the surface with the immunoreagent. It is believed that this process is not suitable for preparation of perfluorocarbon polymer supports because once water is added to a perfluorocarbon polymer carrier, it will become unwetted and float to the water surface. Adsorption of a perfluorocarbon-substituted ligand or binder to the carrier surface could be non-uniform and unsecure.

Applicant's assignee's patents, U.S. Pat. No. 4,885,250 and U.S. Pat. No. 4,954,444 listed above, describe a procedure for preparing solid perfluorocarbon polymer carriers by first contacting the carriers with methanol followed by aqueous methanol, water, and buffer prior to contacting the carriers with aqueous solutions of perfluorocarbon-substituted ligands or binders. While such procedure results in secure binding of ligands or binders, handling of the carriers can be difficult. Upon contacting the carriers with water, they become unwetted and float to the water surface. Small quantities of the carriers can be rewetted by high speed centrifugation, but centrifugation cannot rewet large scale batch quantities of carriers.

There exists a need for a convenient process for preparing solid perfluorocarbon polymer supports permitting uniform and secure adsorption of perfluorocarbon-substituted ligands or binders.

SUMMARY OF THE INVENTION

The process of this invention is a process for preparing a solid perfluorocarbon polymer support comprising the steps of:

(a) contacting a perfluorocarbon polymer carrier with a first water miscible organic solvent capable of wetting said carrier;

(b) separating the carrier from said solvent;

(c) adding an aqueous solution of a second water miscible organic solvent wherein said solution is capable of wetting said carrier;

(d) adding a perfluorocarbon-substituted ligand or binder solution containing said second water miscible organic solvent to said carrier;

provided that neither solution in steps (c) and (d) is at a denaturing concentration for said ligand or binder; and (e) stirring the mixture of step (d) for a time sufficient to allow for secure and uniform attachment of said ligand or binder to said carrier.

DESCRIPTION OF THE INVENTION

The process of this invention is useful for preparing solid perfluorocarbon polymer supports having uniformly and securely attached perfluorocarbon-substituted ligands and binders on solid perfluorocarbon polymer carrier surfaces. By perfluorocarbon is meant a molecule which contains the largest possible or a relatively large proportion of fluorine atoms in its structure. Some perfluorocarbon polymers which can be used in the process of this invention include various Teflon ® fluorocarbon polymers, such as polytetrafluoroethylene, polyvinylfluoride and polyvinylidene difluoride. (Teflon ® is a registered trademark of E. I. du Pont de Nemours and Company.)

Ligands and binders are two components in specific bioaffinity binding pairs. By ligand is meant an antigen, hapten, nucleic acid, enzyme substrate, vitamin, dye or other small organic molecule including enzyme substrates, effectors and inhibitors and by binder is meant an antibody, enzyme, nucleic acid, binding protein, synthetic mimics of binding proteins such as polylysine and polyethyleneimines or other biomacromolecule capable of specific binding, enzyme/substrate, etc. interactions.

To permit selective high affinity (secure) binding of a ligand or binder to the surface of the perfluorocarbon polymer carrier, the ligand or binder is modified by attaching perfluorocarbon groups covalently. The number of perfluorocarbon groups attached to the ligand or binder is defined as the degree of substitution. The degree of substitution required to provide secure attachment to the carrier is expected to vary significantly depending upon the nature of the perfluorocarbon group on the ligand or binder, the size and nature of the ligand or binder, and the eventual use of the support formed. In general, the higher the degree of substitution, the stronger the attachment.

Compounds such as the acid chlorides, anhydrides and imidazolides of various perfluorocarbon acids, for example, perfluorooctanoyl chloride, perfluorooctyl acetyl and propanoyl chlorides and perfluorooctanoyl and perfluorooctyl propanoyl imidazolides have been used successfully to modify ligands and binders. Of these, the imidazolide derivative is preferred due to its lower reactivity allowing more controllable reactions. The most preferred class of compounds is highly fluorinated isocyanates having the formula $R_FCH_2CH_2CH_2NCO$, wherein $R_F$ is a linear, branched or carbocyclic perfluorinated radical containing 1–20 carbon atoms. The isocyanates are most preferred because of their increased stability to hydrolysis at the slightly alkaline reaction conditions generally used during the preparation of the fluorocarbon-substituted ligand or binder. A specifically preferred compound is $F(CF_2)_8CH_2CH_2CH_2NCO$.

The modification reactions are carried out by mixing an aqueous solution of the ligand or binder with the fluorinated reagent dissolved in a water miscible organic solvent under controlled time, temperature and pH conditions. Many water miscible organic solvents can be used to dissolve the fluorinated reagent, for example, dioxane, tetrahydrofuran, and acetonitrile. Because the fluorinated reagents useful for modifying ligands and binders can react with alcohols, alcohols are not useful for dissolving the fluorinated reagent. Acetonitrile is preferred since it contains no peroxide impurities, which can cause the ligand or binder to oxidize.

The process of the instant invention is performed by contacting a perfluorocarbon polymer carrier with a first water miscible organic solvent, separating the carrier, followed by adding an aqueous solution of a second water miscible organic solvent prior to contacting the carrier with a perfluorocarbon-substituted ligand or binder solution containing the second water miscible organic solvent.

Specifically, the perfluorocarbon polymer carrier is contacted with a first water miscible organic solvent which wets the carrier surface. It is believed that by wetting the carrier surface, an air layer which can hinder perfluorocarbon-substituted ligand or binder from contacting the carrier surface directly is displaced by the solvent. Carrier which is unwetted will float in aqueous solution. Various water miscible organic solvents can be used to wet the carrier surface. Such solvents include alcohols, such as methanol and n-butanol, dioxane, acetonitrile, tetrahydrofuran, and dimethylformamide. Methanol is preferred. Usually, neat solvent is used to wet the carrier initially. However, a solution containing a high concentration of solvent can also be used so long as the concentration of solvent is sufficiently high to wet the carrier. Such solution can be solvent dissolved in water or solvent dissolved in another water miscible organic solvent.

Once the perfluorocarbon polymer carrier is wetted with a first water miscible organic solvent, the carrier is separated from the organic solvent. Since solutions containing a high concentration of organic solvent can denature perfluorocarbon-substituted ligands and binders, the organic solvent and carrier are separated before contacting the carrier with ligand or binder. Separation can be performed by decanting or aspirating the solvent.

An aqueous solution of a second water miscible organic solvent is then added to the wetted carrier. The second water miscible organic solvent is the same as that contained in the perfluorocarbon-substituted ligand or binder solution to be added later in the process. Such solvents include dioxane, tetrahydrofuran and acetonitrile. Acetonitrile is preferred. The first and second solvents can be the same solvent so long as such solvent is the same as that contained in the ligand or binder solution. In the event that alcohol is used as a first water miscible organic solvent, the second water miscible solvent solution can be used to remove any alcohol remaining after separation of alcohol and carrier since such alcohol can denature the perfluorocarbon-substituted ligand or binder. Removal can be accomplished by washing the carrier several times with the second water miscible organic solvent solution.

The perfluorocarbon-substituted ligand or binder solution containing second water miscible organic solvent is then added to the carrier. The solvent contained in both the solution added to the carrier and the ligand or binder solution must not be at a denaturing concentration. By a denaturing concentration is meant a concentration of solvent which causes the ligand or binder to lose its native conformation. Additionally, the concentration of solvent in the first of such solutions containing second water miscible organic solvent must be sufficient to maintain a wetted carrier. It is recommended that the concentration of solvent in both solutions be less than approximately 50% v/v solvent to aqueous buffer solution. A concentration of approximately 16% v/v solvent to buffer solution is preferred.

The resulting mixture of carrier and perfluorocarbon-substituted ligand or binder is stirred gently for a time sufficient to allow for uniform and secure attachement of the ligand or binder to the carrier surface. Uniform and secure attachment can usually be achieved in one hour. It is important to stir the mixture gently so as not to cause foaming and aeration. It is believed that foaming and aeration can lead to air contacting the carrier surface and the carrier can become unwetted.

One advantage of the process of the instant invention is that the perfluorocarbon polymer supports prepared by this process have a greater number of securely attached perfluorocarbon-substituted ligands and binders on the support surfaces than supports prepared by other methods. Supports prepared by the process of the instant invention have more ligands and binders which are securely attached because only ligands and binders which are highly substituted are adsorbed onto the carrier surface. Previous methods for preparing supports in aqueous solutions required an organic solvent wash after preparing the support to remove loosely bound, insufficiently substituted ligands and binders. The carrier and the organic solvent have a strong affinity for one another; the affinity being stronger than the bond created between the carrier and insufficiently substituted ligands or binders. Consequently, when the support is washed with organic solvent, the solvent displaces such ligands or binders. By adsorbing the ligands and binders to the carrier in organic solvent using the process of this invention, those ligands or binders which are insufficiently substituted will not bind to the carrier and the resulting support will have highly secure ligands and binders attached to its surface without the need for performing an organic solvent wash step.

The following example illustrates the invention:

EXAMPLE 1

Supports Prepared Using Methanol and Tetrahydrofuran

To 0.66 mL of a 75 mg/mL monoclonal antibody solution was added 19.34 mL of 0.1M phosphate buffer, pH 8.5. To the buffered monoclonal antibody solution was added 2.5 mL of a THF solution containing 40 mg/mL of (perfluorooctyl) propanoyl imidazolide. The reaction mixture was stirred at room temperature for approximately one hour, centrifuged at 3000 rpm for 2 minutes, and applied to a 2.5×30 cm column of Bio-Gel ® P6 (Bio-Rad Laboratories, Richmond, CA), equilibrated with 0.05M phosphate buffer, pH 8.0. The perfluorocarbon-substituted monoclonal antibody was eluted in the void volume of the column and was collected. The previous steps were repeated seven times and a total of 300 mL of perfluorocarbon-substituted monoclonal antibody was collected. To this monoclonal antibody solution was added 100 mL of 0.05M phosphate buffer, ph 8.0 and 40 mL of THF. Spectrophotometric analyis of the monoclonal antibody solution showed that the amount of substituted antibody present for adsorption to a carrier surface was 364 mg.

One hundred grams of Perflex TM 75s, a powdered perfluorocarbon polymer carrier, was weighed into each of four 500-mL polycarbonate centrifuge tubes. To each tube was added 200 mL of methanol. The mixtures were stirred to wet the carrier thoroughly. To each mixture was added 200 mL of water. The carrier was separated from the aqueous methanol by centrifuging the tubes at 3000 rpm for 2 minutes and decanting the supernatants.

To each centrifuge tube was added 200 mL of a solution containing 16% v/v THF in 0.05M phosphate buffer, pH 8.0. The mixtures were stirred to wet the Perflex TM carrier thoroughly and the carrier was separated from the THF solution by centrifuging the tubes at 3000 rpm for 2 minutes and decanting the supernatants.

One hundred ten mL of the perfluorocarbon-substituted monoclonal antibody solution prepared above was added to each centrifuge tube containing wetted Perflex TM carrier. The mixtures were stirred gently for approximately one hour and the tubes centrifuged at 3000 rpm for 2 minutes. The supernatants were decanted, combined and analyzed spectrophotometrically for the amount of substituted monoclonal antibody which was not attached to the carrier. The analysis showed that 39 mg of substituted monoclonal antibody was not attached.

Two hundred fifty mL of 0.05M phosphate buffer, pH 8.0, containing 1% Zonyl ® FSN fluorosurfactant (Zonyl ® is a registered trademark of E.I. du Pont de Nemours and Company, Wilmington, DE) was added to each centrifuge tube. The mixtures were stirred gently for 30 minutes and the tubes were centrifuged at 3000 rpm for 2 minutes. The supernatants were decanted, combined and analyzed spectrophotometrically for the amount of perfluorocarbon-substituted monoclonal antibody which was removed by Zonyl ® FSN. The analysis showed that 29 mg of substituted monoclonal antibody was washed off by Zonyl ® FSN indicating that greater than 90% of the substituted monoclonal antibody which had been attached to the carrier was attached securely.

The Perflex TM support having perfluorocarbon-substituted monoclonal antibody attached to its surface was packed into a chromatographic column and the column was percolated with 0.05M phosphate buffer, pH 8.0, to wash off excess Zonyl ® FSN and any perfluorocarbon-substituted monoclonal antibody not attached securely to the carrier. The eluants were collected, combined and analyzed spectrophotometrically for the amount of substituted monoclonal antibody removed. The analysis showed that 18 mg of substituted monoclonal antibody had been removed from the support.

The total amount of perfluorocarbon-substituted monoclonal antibody securely attached to the Perflex ™ carrier was determined by subtracting the amounts of substituted monoclonal antibody which were removed by Zonyl® FSN and phosphate buffer from the amount of substituted monoclonal antibody added to the carrier. The total amount of perfluorocarbon-substituted monoclonal antibody securely attached to the support was determined to be 278 mg. Therefore, the loading of substituted monoclonal antibody onto the carrier was approximately 0.7 mg of substituted monoclonal antibody per gram of carrier.

The perfluorocarbon polymer support prepared by the process of the instant invention wherein the carrier remained wetted throughout the process resulted in a greater amount of securely attached perfluorocarbon-substituted monoclonal antibody on the support surface than could have been obtained by a process using only one water miscible organic solvent wherein the carrier became unwetted during the process. Additionally, because the carrier remained wetted throughout the process, it was easier to handle.

EXAMPLE 2

Supports Prepared using Methanol and Acetonitrile

A 10 mg/mL monoclonal antibody solution was diluted to 2 mg/mL by adding 140 mL of 0.1M sodium phosphate buffer, pH 8.5, to 35 mL of monoclonal antibody solution. Thirty-five mL of an acetonitrile solution containing 5 µL of perfluoroctylpropyl isocyanate was added to the monoclonal antibody solution and the mixture was stirred at room temperature for 90 minutes.

Fifty grams of Perflex ™ carrier was weighed into each of three 250-mL polypropylene centrifuge bottles. To each bottle was added 75 mL of methanol, followed by 75 mL of water. The mixtures were stirred, the tubes were centrifuged at 2000 rpm for 2 minutes and supernatants were decanted.

One hundred mL of a solution containing 16% v/v acetonitrile in 0.1M sodium phosphate buffer, pH 8.5, was added to each centrifuge bottle. The mixtures were stirred gently, the tubes were centrifuged at 2000 rpm for 2 minutes and supernatants were decanted. The preceding steps were repeated to ensure removal of all methanol.

Thirty mL of perfluorocarbon-substituted monoclonal antibody prepared above was added to one of the centrifuge bottles containing wetted Perflex ™ carrier. The mixture was stirred gently while the total volume was brought to 120 mL with phosphate buffer. The mixture was stirred gently at room temperature for one hour and transferred to a coarse fritted filter funnel. The mixture was percolated with 400 mL phosphate buffer, followed by 250 mL of a 0.5% solution of Zonyl® FSN and 250 mL of phosphate buffer. All eluants were collected for analysis of the amount of unattached substituted monoclonal antibody. Supports were prepared from the remaining two samples of wetted carrier by adding 60 mL and 120 mL, respectively, of the perfluorocarbon-substituted monoclonal antibody solution and following the same steps described above. All eluants were collected for analysis of the amount of unattached substituted monoclonal antibody.

The eluants were analyzed spectrophotometrically and the loading of perfluorocarbon-substituted monoclonal antibody onto the Perflex ™ carrier was determined for each of the three supports prepared. The loadings were 0.77, 1.27 and 2.70 mg, respectively, of perfluorocarbon-substituted monoclonal antibody per gram of carrier.

I claim:

1. A process for attaching a perfluorocarbon-substituted ligand or binder to a perfluorocarbon polymer carrier comprising the steps of:
   (a) contacting a perfluorocarbon polymer carrier with a first neat water miscible organic solvent capable of wetting said carrier to produce a wetted carrier;
   (b) separating said wetted carrier from said solvent;
   (c) adding an aqueous solution of a second water miscible organic solvent to said wetted carrier wherein said solution is capable of wetting said carrier;
   (d) adding a perfluorocarbon-substituted ligand or binder solution containing said second water miscible organic solvent to said wetted carrier;
   provided that neither solution in steps (c) and (d) is at a denaturing concentration for said ligand or binder; and
   (e) stirring the mixture of step (d) to allow for secure and uniform attachment of said ligand or binder to said wetted carrier.

2. The method of claim 1 wherein the first water miscible organic solvent is selected from the group consisting of alcohol, dioxane, acetonitrile, tetrahydrofuran and dimethylformamide.

3. The method claim 2 wherein the alcohol is methanol.

4. The method of claim 1 wherein the second water miscible organic solvent is selected from the group consisting of dioxane, acetonitrile, tetrahydrofuran and dimethylformamide.

* * * * *